(12) United States Patent
Nishimizu et al.

(10) Patent No.: US 7,235,967 B2
(45) Date of Patent: Jun. 26, 2007

(54) EDDY CURRENT TESTING PROBE AND EDDY CURRENT TESTING APPARATUS

(75) Inventors: Akira Nishimizu, Tokai (JP); Tetsuya Matsui, Hitachi (JP); Masahiro Koike, Hitachi (JP); Yoshio Nonaka, Hitachi (JP); Isao Yoshida, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 17 days.

(21) Appl. No.: 11/326,510

(22) Filed: Jan. 6, 2006

(65) Prior Publication Data
US 2006/0170420 A1  Aug. 3, 2006

(30) Foreign Application Priority Data
Jan. 12, 2005 (JP) .............................. 2005-004898

(51) Int. Cl.
*G01R 33/12* (2006.01)
(52) U.S. Cl. ...................... 324/239; 324/238; 324/262; 324/243
(58) Field of Classification Search ........ 324/228–243, 324/262
See application file for complete search history.

(56) References Cited

U.S. PATENT DOCUMENTS

| 4,810,966 | A | * | 3/1989 | Schmall ................. 324/207.11 |
| 5,315,234 | A | * | 5/1994 | Sutton et al. ............... 324/242 |
| 6,150,809 | A | * | 11/2000 | Tiernan et al. .............. 324/238 |
| 6,339,326 | B1 | | 1/2002 | Trantow |
| 6,670,808 | B2 | * | 12/2003 | Nath et al. .................. 324/230 |
| 2003/0025496 | A1 | | 2/2003 | Trantow et al. |
| 2003/0155914 | A1 | | 8/2003 | Tsukernik et al. |

FOREIGN PATENT DOCUMENTS

| JP | 2002-201961 | 7/2002 |
| JP | 2003-344360 | 12/2003 |

* cited by examiner

*Primary Examiner*—Jay M. Patidar
(74) *Attorney, Agent, or Firm*—Mattingly, Stanger, Malur & Brundidge, P.C.

(57) ABSTRACT

An eddy current testing probe has a flexible substrate adapted to face to a surface of a test article, a plurality of coils which are fixed to the flexible substrate and energized one of which is capable of being changed sequentially, a pressing member for pressing the substrate toward the test article, an elastic member arranged between the substrate and the pressing member, and a movement limiting member for limiting a movement of the pressing member toward the test article.

13 Claims, 12 Drawing Sheets

FIG.5
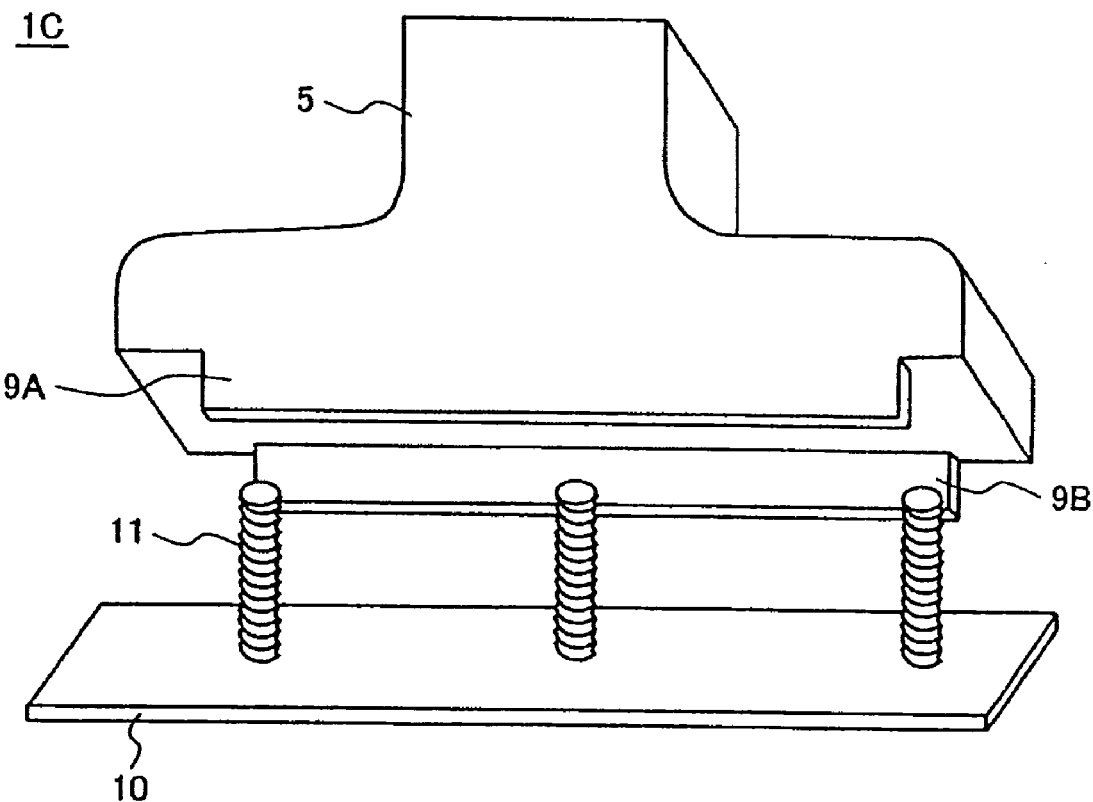
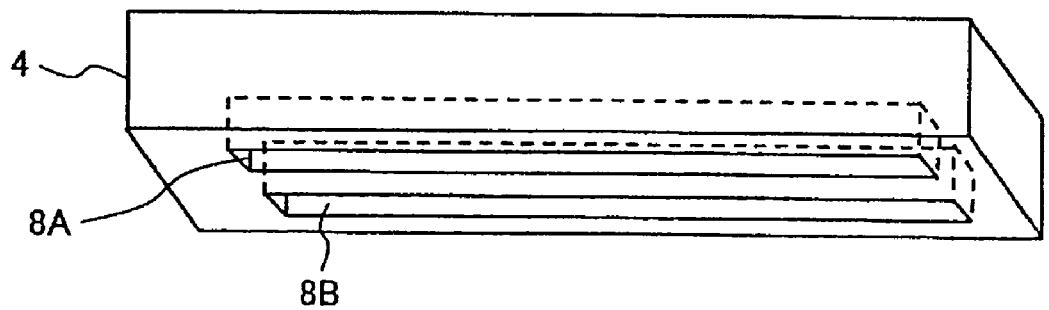
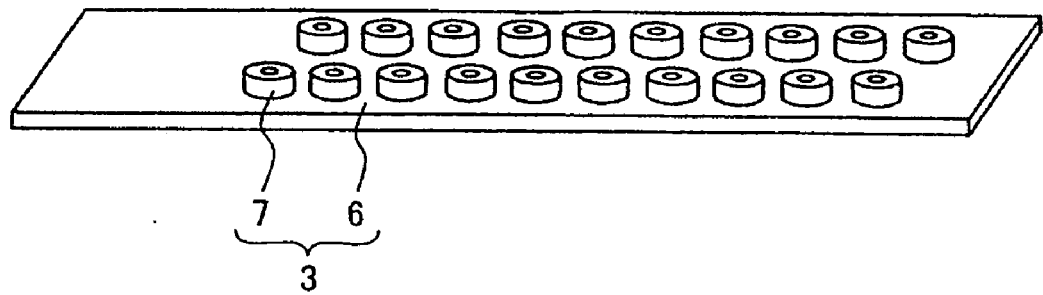

EDDY CURRENT TESTING PROBE AND EDDY CURRENT TESTING APPARATUS

BACKGROUND OF THE INVENTION

The present invention relates to an eddy current testing probe and eddy current testing apparatus, particularly to an eddy current testing probe and eddy current testing apparatus for detecting a flaw in a test article by changing sequentially energized one(s) of a plurality of coils to detect a flaw signal generated by a detecting coil.

The eddy current testing probe and eddy current testing apparatus for detecting the flaw in the test article by changing sequentially energized one(s) of the plurality of coils to detect the flaw signal generated by the detecting coil, was already provided as shown by, for example, JP-A-2003-344360.

That is, in these, the plurality of coils are arranged on a flexible substrate so that the coils are pressed against a surface of the test article by an elasticity such as a leaf spring or the like, and under this situation, energized one(s) of the coils is sequentially changed to detect the flaw in the test article from the flaw signal generated by the detecting coil.

BRIEF SUMMARY OF THE INVENTION

In the eddy current testing probe described in JP-A-2003-344360, there is a probability of that the coils are deformed by a force generated by the elastic member such as leaf spring or the like to press the coils against the test article. If the coils are deformed by the pressing force, the eddy current of designed value cannot be applied correctly to the test article and the generated eddy current cannot be measured correctly so that the flaw detection cannot be performed correctly.

An object of the present invention is to provide an eddy current testing probe and eddy current testing apparatus, by which coils without deformation thereof can be pressed against a test article.

Another object of the present invention is to provide an eddy current testing probe and eddy current testing apparatus, by which a flaw can be correctly detected.

For accomplishing the above objects, an eddy current testing probe has a flexible substrate adapted to face to a surface of a test article, a plurality of coils which are fixed to the flexible substrate and energized one of which is capable of being changed sequentially, a pressing member for pressing the substrate toward the test article, an elastic member arranged between the substrate and the pressing member (so that the substrate is pressed against the surface of the test article through the elastic member by the pressing member), and a movement limiting member for limiting a movement of the pressing member toward the test article.

In the above eddy current testing probe, since a deformation of the elastic member caused by the pressing member is limited by the movement limiting member, the coils are prevented from being deformed by the pressing member through the elastic member so that a flaw detection can be performed correctly without the deformation of the coils.

As explained above, the eddy current testing probe and eddy current testing apparatus in which the flaw detection can be performed correctly without the deformation of the coils are obtainable.

Other objects, features and advantages of the invention will become apparent from the following description of the embodiments of the invention taken in conjunction with the accompanying drawings.

BRIEF DESCRIPTION OF THE SEVERAL VIEWS OF THE DRAWINGS

FIG. 5 is an oblique projection exploded view showing a fourth embodiment of eddy current testing probe of the invention.

DETAILED DESCRIPTION OF THE INVENTION

Figure 1:
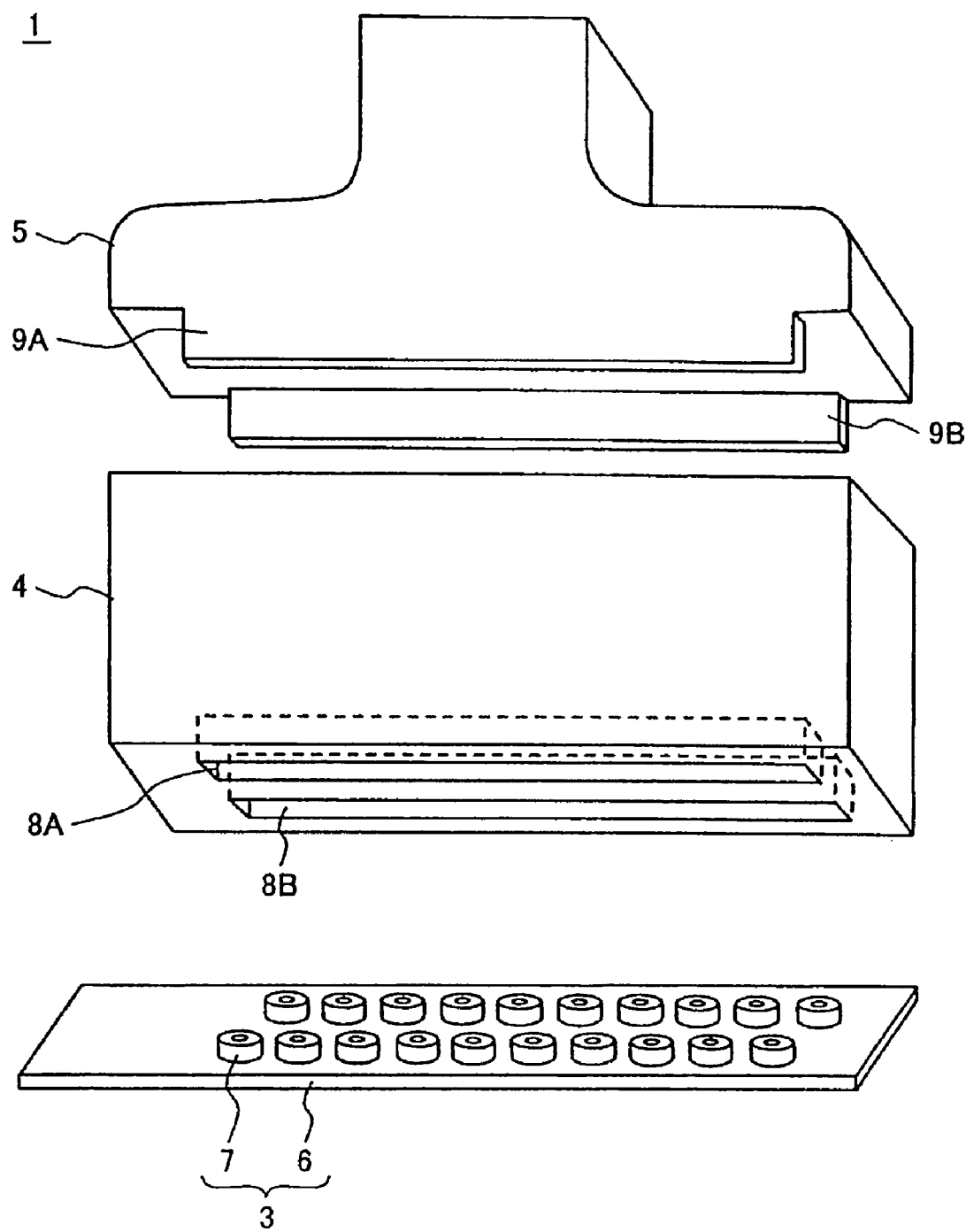
FIG. 1 is an oblique projection exploded view showing a first embodiment of eddy current testing probe of the invention.
Figure 2:
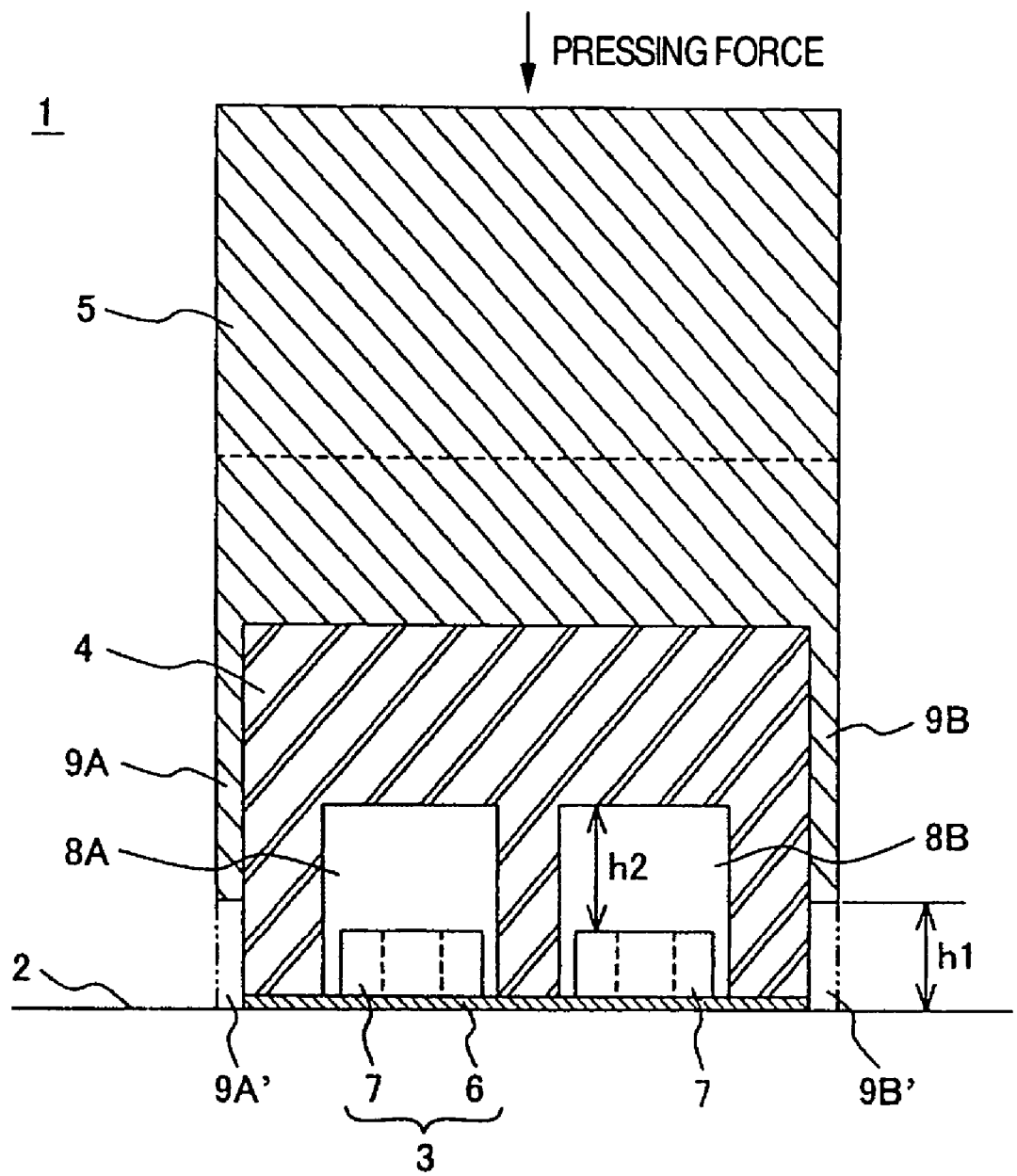
FIG. 2 is an enlarged cross sectional view of the eddy current testing probe shown in FIG. 1.

Hereafter, a first embodiment of eddy current testing probe of the invention is explained on the basis of FIGS. 1 and 2.

An eddy current testing probe 1 includes a flaw detection sensor 3 for facing to a surface of a test article 2, an elastic member 4 for pressing the flaw detection sensor 3 against the test article 2, and a pressing member 5 for pressing the elastic member 4 so that the flaw detection sensor 3 is pressed against the test article 2.

The flaw detection sensor 3 includes a flexible substrate 6 including a stack of films of, for example, polyimide, and a plurality of coils 7 fixed along single direction to the flexible substrate 6 through an adhesive or the like having flexibility after being cured in such a manner that the flexible substrate 6 is arranged between the coils 7 and the test article 2. In this embodiment, the coils 7 form two rows, and electric wires (not shown) connected to the coils 7 respectively extend between the polyimide films in the stack.

The elastic member 4 has a rectangular shape formed of sponge of, for example, polyurethane rubber, and including coil receiving grooves 8A and 8B for containing respectively the two rows of the coils mounted on the flexible substrate 6.

The pressing member 5 is made of, for example, bakelite, aluminum or the like and is capable of pressing the elastic member 4 toward the test article 2. The pressing member 5 has protruding parts 9A and 9B as the claimed movement limiting member protruding toward the test article 2 from a contact position between the pressing member 5 and elastic member 4.

The flaw detection sensor 3, elastic member 4 and pressing member 5 are combined with each other by well-known means such as adhesive, screw, engagement or the like so that a handling of them is easy. When the eddy current testing probe 1 is pressed against the test article 2, a dimension h1 from front ends of the protruding parts 9A and 9B to the test article 2 and a dimension h2 from the coils 7 to bottoms of the coil receiving grooves 8A and 8B satisfy h1≦h2.

When the flaw of the test article 2 having a substantially planar surface is detected by the above mentioned eddy current testing probe 1, the flexible substrate 6 is pressed by the pressing member 5 against the surface of the test article 2. In this situation, the elastic member 4 is deformed by the pressing force of the pressing member 5 so that the flexible substrate 6 is deformed along the surface of the test article 2 to contact the surface of the test article 2. When the front ends of the protruding parts 9A and 9B of the pressing member 5 contact the test article 2 as shown by the protruding parts 9A' and 9B' of two-dot chain lines, the energized one of the coils 7 is changed sequentially along the rows to excite magnetically and detect an eddy current so that the flaw in the test article 2 is detectable. Incidentally, since h1≦h2 is satisfied when the front ends of the protruding parts 9A and 9B of the pressing member 5 contact the test article 2, the coils 7 are prevented from contacting the bottoms of the coil receiving grooves 8A and 8B or prevented from being compressed by a force sufficient for deforming the coils 7 even when the coils 7 contact the bottoms of the coil receiving grooves 8A and 8B.

As explained above, in the embodiment, even when a great pressing force is applied, the force sufficient for deforming the coils 7 is prevented by the protruding parts 9A and 9B of the pressing member 5 from being applied to the coils 7 so that the flaw can be detected correctly.

Although the eddy current testing probe 1 of the embodiment is usable for the substantially planar surface of the test article 2, it is usable for the flaw detection in a case where the surface of the test article 2 has a slightly curved shape of curvature tolerable by the elastic member 4.

Figure 3:
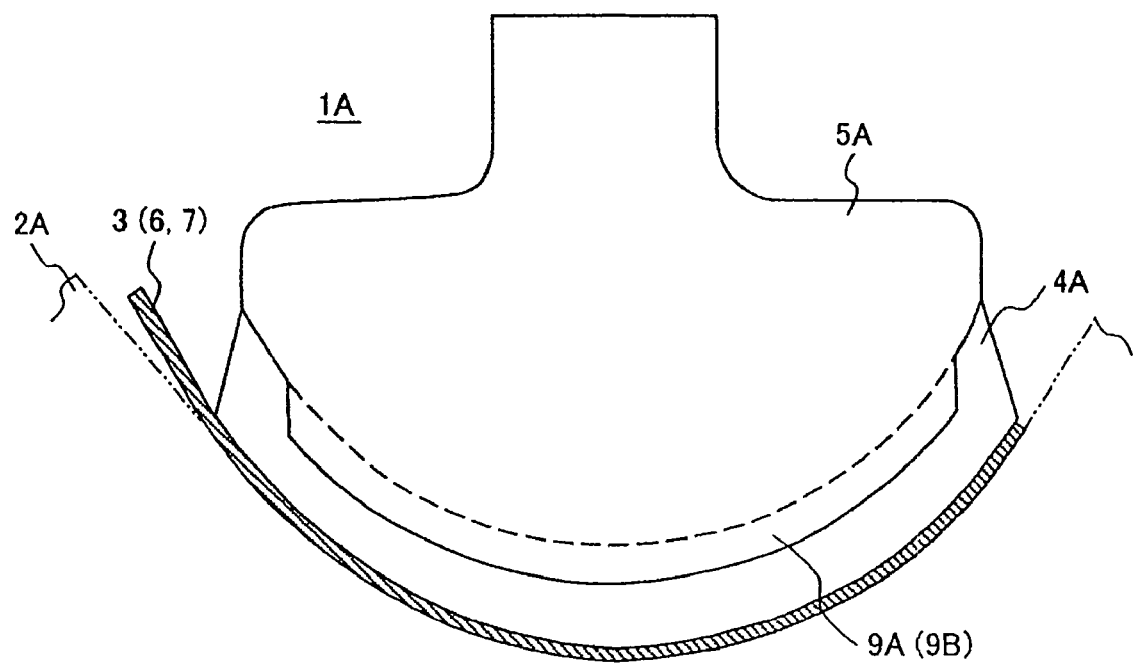
FIG. 3 is a side view showing a second embodiment of eddy current testing probe of the invention.

FIG. 3 shows a second embodiment of the invention, and the eddy current testing probe 1A shown therein is usable for a case where the surface of the test article 2 has a concave curved shape. The eddy current testing probe 1A has an elastic member 4A previously curved, a flaw detection sensor 3 including the flexible substrate 6 fixed by the adhesive or the like to a convex surface of the elastic member 4A, the pressing member 5A including a convex surface adhered to a concave surface of the elastic member 4A, and the protruding parts 9A and 9B extending from the pressing member 5A toward the elastic member 4A and having curved surfaces of the same curvature as the pressing member 5A. Incidentally, the elastic member 4A has coil receiving grooves (not shown) facing to the detection sensor 3 to receive respectively the coils 7 of the flaw detection sensor 3, and the basic structure of the eddy current testing probe 1A has the same structure as the eddy current testing probe 1 of the first embodiment.

By the eddy current testing probe 1A, the flaw can be detected in the test article 2A having the concave surface which is not tolerable by the eddy current testing probe 1 of the first embodiment. Further, since the curved protruding parts 9A and 9B limit the pressing force from the pressing member 5A similarly to the first embodiment, the coils 7 of the flaw detection sensor 3 is prevented from being deformed or damaged, so that the flaw can be detected correctly.

Figure 4:
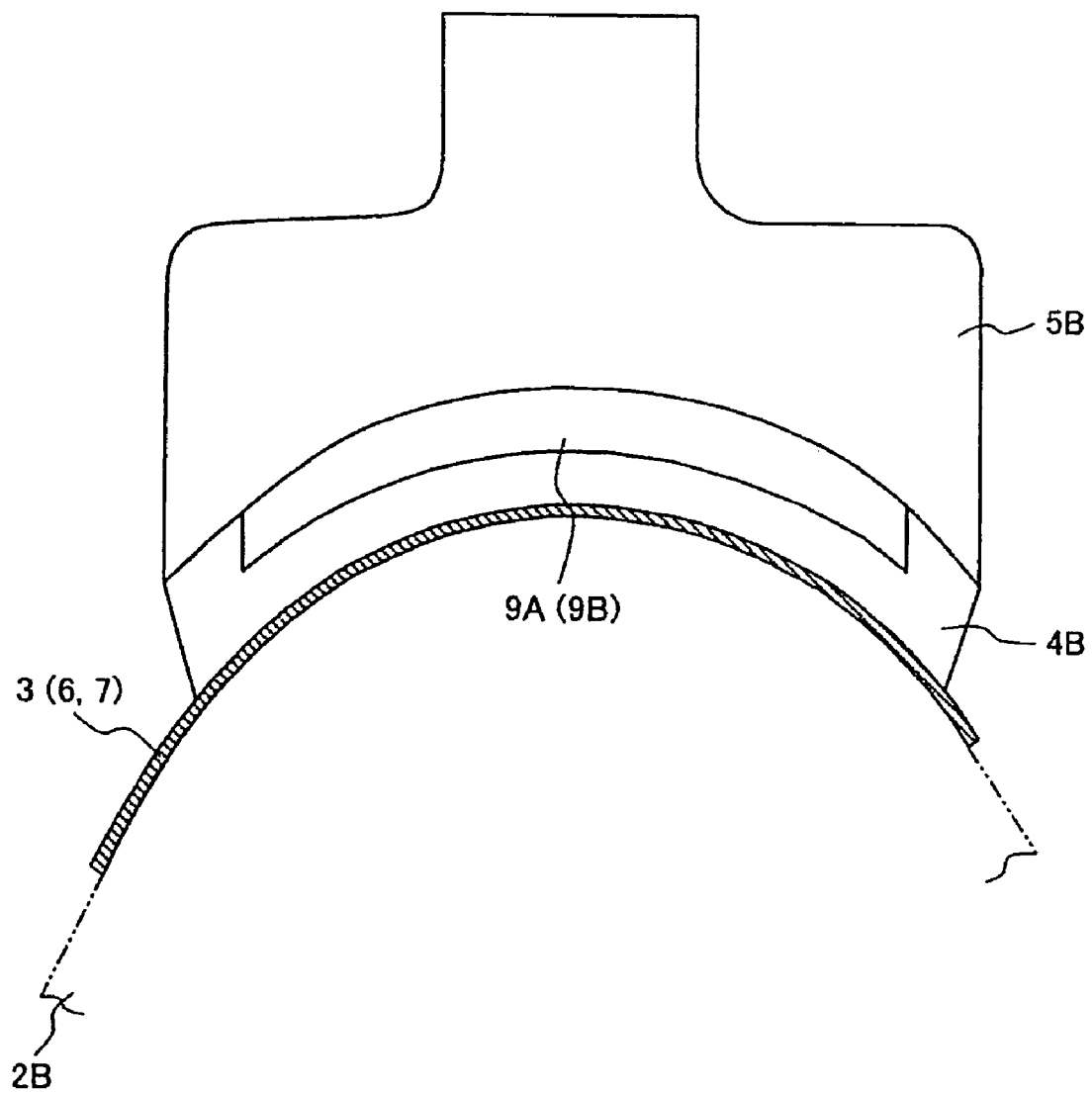
FIG. 4 is a side view showing a third embodiment of eddy current testing probe of the invention.

FIG. 4 shows a third embodiment of the invention, and the eddy current testing probe 1B shown therein is usable for a case where the surface of the test article 2B has a convex curved shape. The eddy current testing probe 1B has an elastic member 4B previously curved, the flaw detection sensor 3 including the flexible substrate 6 fixed by the adhesive or the like to a concave surface of the elastic member 4B, the pressing member 5A including a concave surface adhered to a convex surface of the elastic member 4B, and the protruding parts 9A and 9B extending from the pressing member 5B toward the elastic member 4B and having curved surfaces of the same curvature as the pressing member 5B. Incidentally, the elastic member 4B has coil receiving grooves (not shown) facing to the detection sensor 3 to receive respectively the coils 7 of the flaw detection sensor 3, and the basic structure of the eddy current testing probe 1B has the same structure as the eddy current testing probe 1 of the first embodiment.

By the eddy current testing probe 1B, the flaw can be detected in the test article 2A having the convex surface which is not tolerable by the eddy current testing probe 1 of the first embodiment. Further, since the curved protruding parts 9A and 9B limit the pressing force from the pressing member 5B similarly to the first embodiment, the coils 7 of the flaw detection sensor 3 is prevented from being deformed or damaged, so that the flaw can be detected correctly.

The eddy current testing probe 1, 1A and 1B are usable in gaseous or liquid environment. If the eddy current testing probe 1, 1A and 1B are used in the liquid environment, the elastic members 4, 4A and 4B of the polyurethane rubber including independently-closed gaseous bubbles shrinks in size by the hydraulic pressure compressing the gaseous bubbles. The decrease in size of the gaseous bubbles causes a decrease of flexibility of the sponge so that the elastic members 4, 4A and 4B cannot absorb the variation of the surface shape of the test articles 2, 2A and 2B to restrain the flaw from being detected correctly.

Therefore, when the eddy current testing probe 1, 1A and 1B are used in liquid environment, it is preferable for the sponge as the elastic members 4, 4A and 4B to prevent the closed gaseous bubbles from being included and to include through holes through which the liquid can flow.

In the above embodiments, the flaw detection sensor 3, the elastic member 4, 4A or 4B and the pressing member 5, 5A or 5B are combined with each other. Therefore, the eddy current testing probes 1, 1A and 1B including the respective elastic members 4, 4A and 4B need to be prepared to correspond to the surfaces of the test articles 2, 2A and 2B respectively. However, preparing the parts for respective situations causes a decrease of yield ratio and an increase of production cost for the eddy current testing probes 1, 1A and 1B.

Figure 6:
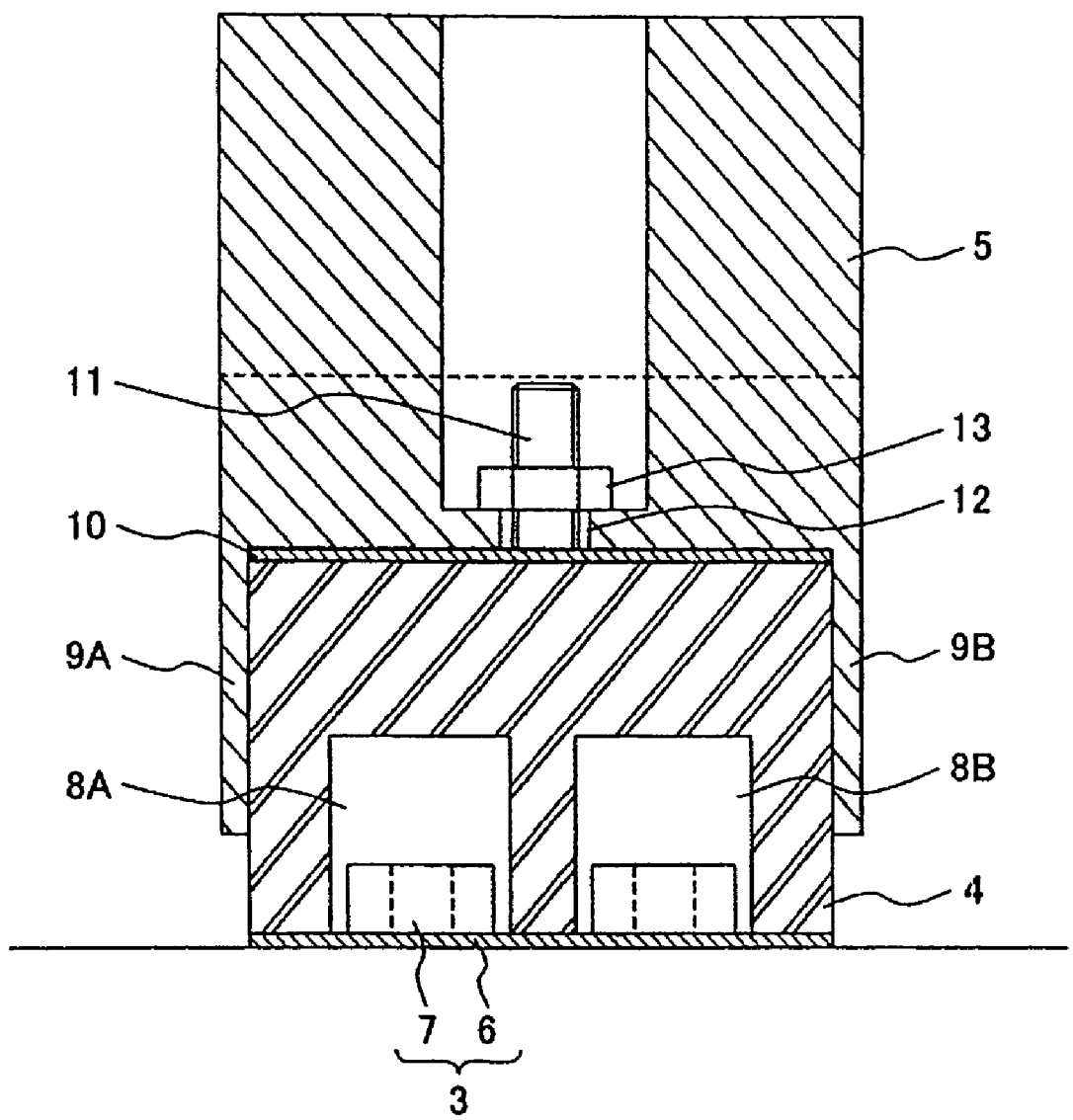
FIG. 6 is an enlarged cross sectional view of the eddy current testing probe shown in FIG. 5.

The eddy current testing probe 1C as the fourth embodiment of the invention as shown in FIGS. 5 and 6 solves these problems. In the eddy current testing probe 1C, the flaw detection sensor 3 of the same structure as the above embodiments is mounted on the elastic member 4 as the rectangular sponge of polyurethane or the like in such a manner that the flaw detection sensor 3 is arranged between the elastic member 4 and the test article 2, and a flexible thin plate 10 of stainless steel or the like having thickness of, for example, 0.1 mm is attached to the elastic member 4 in such a manner that the flexible thin plate 10 is arranged between the elastic member 4 and the pressing member 5. Bolts 11 are fixed to a surface of the flexible thin plate 10 opposite to the elastic member 4. On the other hand, the pressing member 5 has bolt holes 12 through which the bolts 11 extend so that the combined flexible thin plate 10, elastic member 4 and flaw detection sensor 3 are fixed by screwing nuts 13 onto the bolts.

By detachably attaching the elastic member 4 and flaw detection sensor 3 to the pressing member 5 and changing the pressing member in accordance with the variation in shape of the surface of the test article 2, the flaw detection sensor 3 can contact closely the surface of the test article 2.

That is, the eddy current testing probe 1C as shown in FIGS. 5 and 6 with the flat mounting surface of the pressing member 5 for the elastic member 4 can detect the flaw in the test article 2 with the flat surface.

Figure 7:
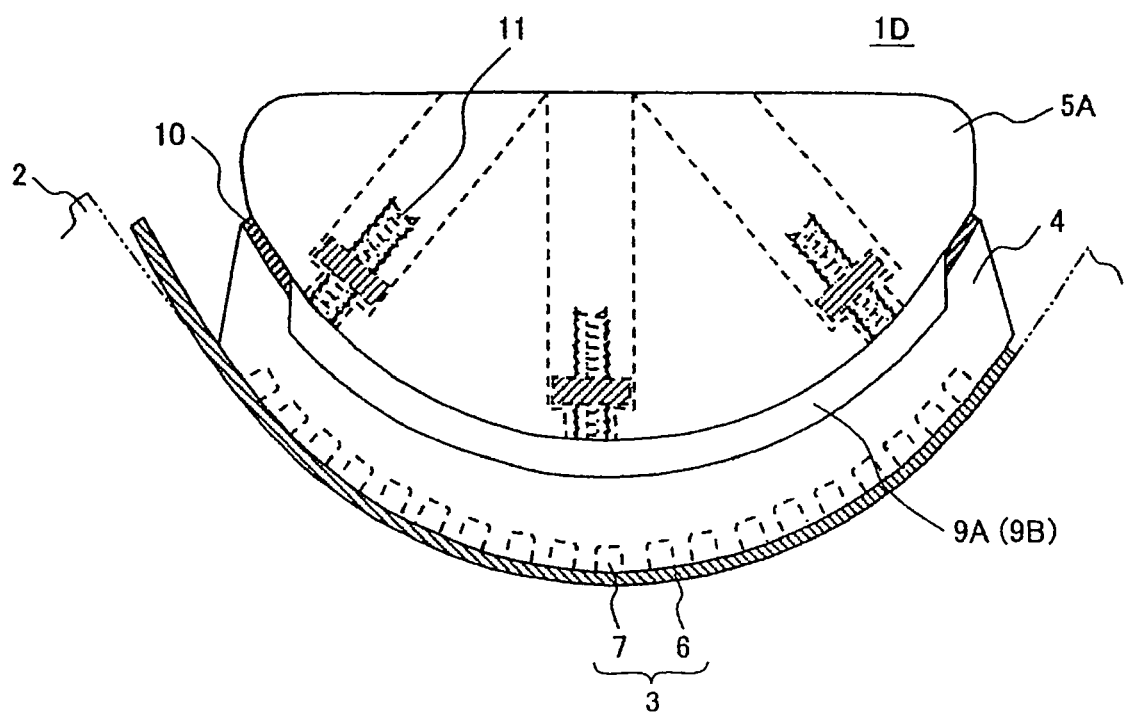
FIG. 7 is a side view showing a fifth embodiment of eddy current testing probe of the invention.

When the test article 2 has the concave surface, as shown in FIG. 7 of the fifth embodiment of the invention, the elastic member 4 and flaw detection sensor 3 are mounted through the flexible thin plate 10 onto the pressing member 5A as a substitute for the pressing member 5, which pressing member 5A has a convex shape on a surface thereof facing to the elastic member 4. By this attaching manner to the pressing member 5A, the flexible thin plate 10 is curved along the convex surface of the pressing member 5A, so that the elastic member 4 and flaw detection sensor 3 combined with the flexible thin plate 10 are curved to form the eddy current testing probe 1D corresponding to the concave surface of the test article 2.

Figure 8:
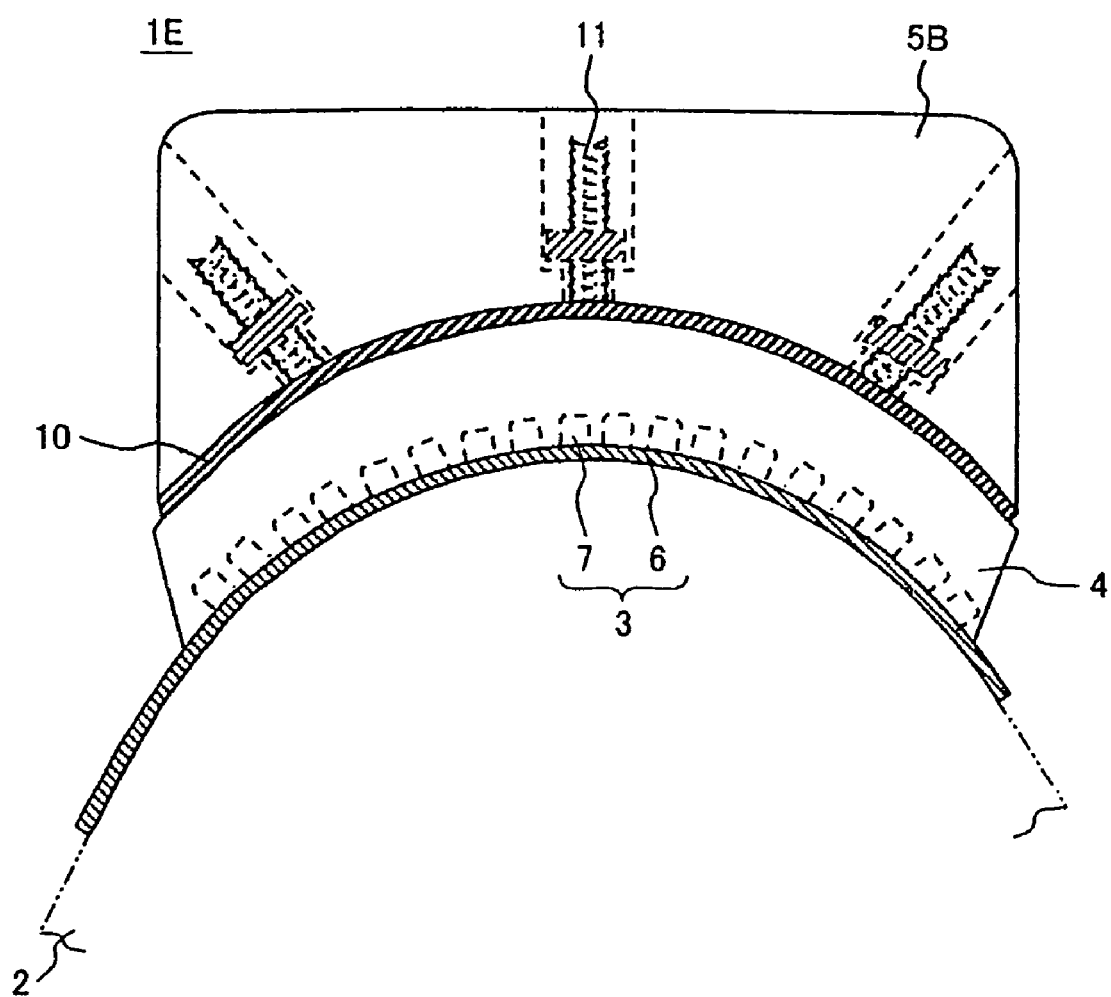
FIG. 8 is a side view showing a sixth embodiment of eddy current testing probe of the invention.
Figure 9:
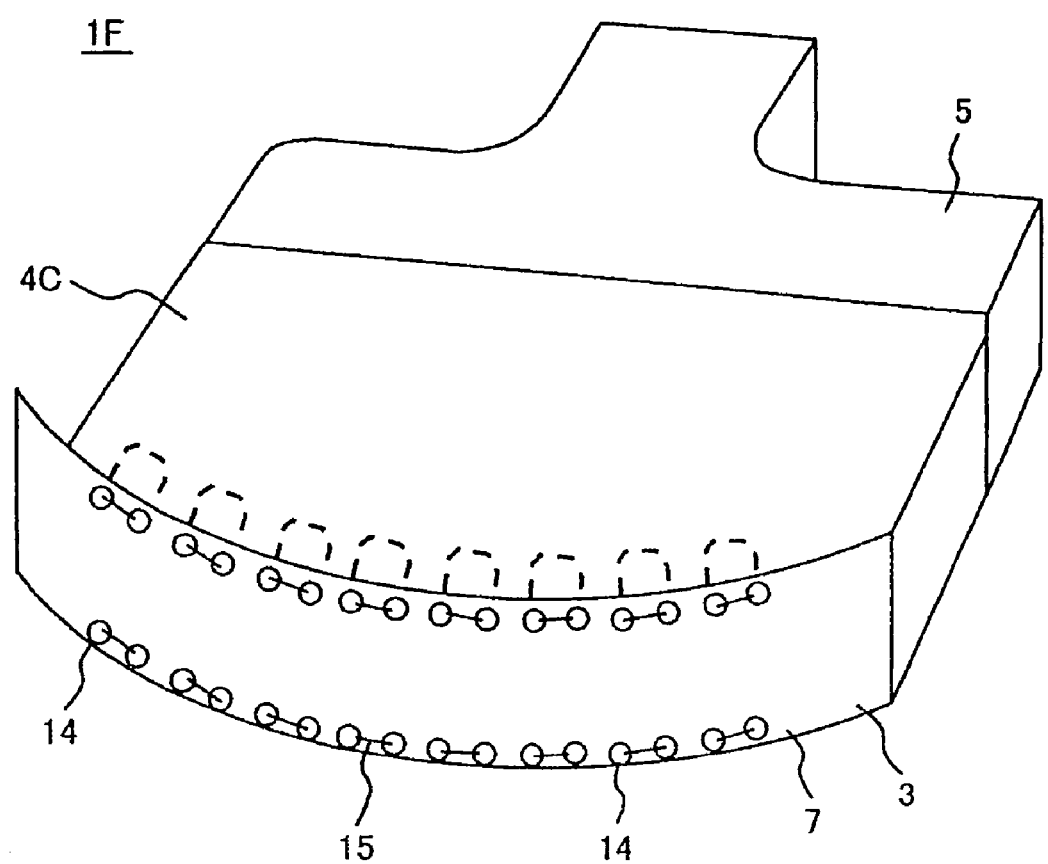
FIG. 9 is an oblique projection view showing a seventh embodiment of eddy current testing probe of the invention.

On the other hand, when the test article 2 has the convex surface, as shown in FIG. 8 of the sixth embodiment of the invention, the elastic member 4 and flaw detection sensor 3 are mounted through the flexible thin plate 10 onto the pressing member 5B as a substitute for the pressing member 5, which pressing member 5B has a concave shape on a surface thereof facing to the elastic member 4. By this attaching manner to the pressing member 5B, the flexible thin plate 10 is curved along the concave surface of the pressing member 5B, so that the elastic member 4 and flaw detection sensor 3 combined with the flexible thin plate 10 are curved to form the eddy current testing probe 1E corresponding to the convex surface of the test article 2.

In the above embodiments, the flexible thin plate 10 is adhered to the elastic members 4, 4A and 4B. However, the adhesion causes an uneconomical replacement of the eddy current testing probe or the combined flexible thin plate 10, elastic member 4 and flaw detection sensor 3 when one of the elastic member 4 and flaw detection sensor 3 is damaged to be replaced. Further, when the adhesive is deteriorated by a long term use to cause a removal of the flaw detection sensor 3 from the elastic member 4, the adhesion process needs to be done again by removing the previous adhesion before coating with the adhesive so that a severe work is necessary.

Therefore, as shown in gig. 9 for the seventh embodiment, in the eddy current testing probe 1F, the elastic member 4 and flaw detection sensor 3 are detachable from each other to solve completely the above problem.

That is, the coils of the flexible substrate 7 included by the flaw detection sensor 3 are not fixed, but the coils of the flexible substrate 7 and the elastic member 4C are seamed together through holes 14 formed on edge portions where the electric wires are not arranged.

By this structure, the problem caused by the adhesion is solved, and only one of the elastic member 4C and flaw detection sensor 3 may be replaced without an uneconomical replacement of both of them when the one of the elastic member 4C and flaw detection sensor 3 is damaged.

In FIGS. 1–9, the members denoted by a common reference symbol have the identical structure. Further, the elastic members 4, 4A, 4B and 4C are made of sponge of polyurethane in the above explanation, however, may be rubber members of non-sponge type, coil springs or the like. Further, although the protruding parts 9A and 9B as the claimed movement limiting member are connected to the pressing member 5, 5A or 5B in the above embodiment, members corresponding to the protruding parts 9A and 9B may be connected to the surface or interior of the elastic member 4, 4A, 4B or 4C, or a dedicated movement limiting member may be used. Incidentally, the movement limiting member prevents effectively the deformation of the coils so that it is also a coil deformation preventing member, and the coil deformation preventing member may be the coil receiving grooves 8A and 8B formed in the elastic member 4, 4A, 4B or 4C and having depth sufficient for preventing the elastic member 4, 4A, 4B or 4C from contacting the coils 7 when the elastic member is deformed.

Figure 10:
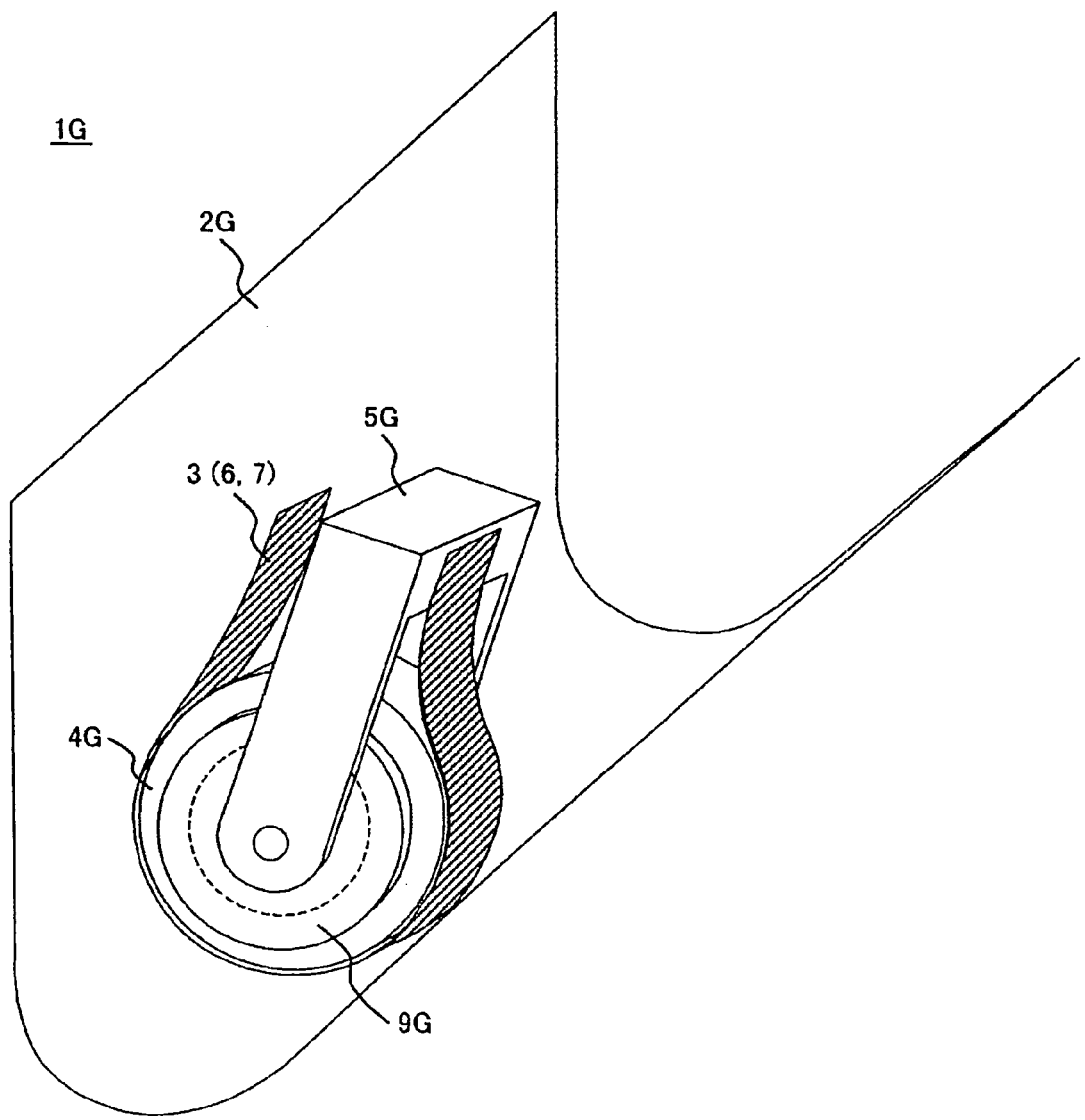
FIG. 10 is a side view showing an eighth embodiment of eddy current testing probe of the invention.

FIG. 10 shows the eighth embodiment in which the eddy current testing probe 1G is usable for detecting the flaw in the test article having a concave surface of narrow angle. The eddy current testing probe 1G has an elastic member 4G of roller shape having a coil receiving groove (not shown) on its outer periphery, the flaw detecting sensor 3 mounted onto the outer periphery of the elastic member 4G through adhesive or the like, disk-shaped protruding parts 9G arranged at both sides of the elastic member 4G and having outer diameters smaller than an outer diameter of the elastic member 4G, and a pressing member 5G supporting coaxially the elastic member 4G and the disk-shaped protruding parts 9G.

By urging the pressing member 5G of the above eddy current testing probe 1G, the pressing member 5G presses through the-elastic member 4G the flaw detecting sensor 3 against the concave surface of the test article 2G. When the elastic member 4G is deformed to a certain extent by the pressing member 5G, the disk-shaped protruding parts 9G contact the surface of the test article 2G so that the elastic member 4G is prevented from being further deformed, whereby the deformation or damage of the coils (not shown) of the flaw detecting sensor 3 is prevented from being caused by a significant deformation of the elastic member 4G.

Figure 11:
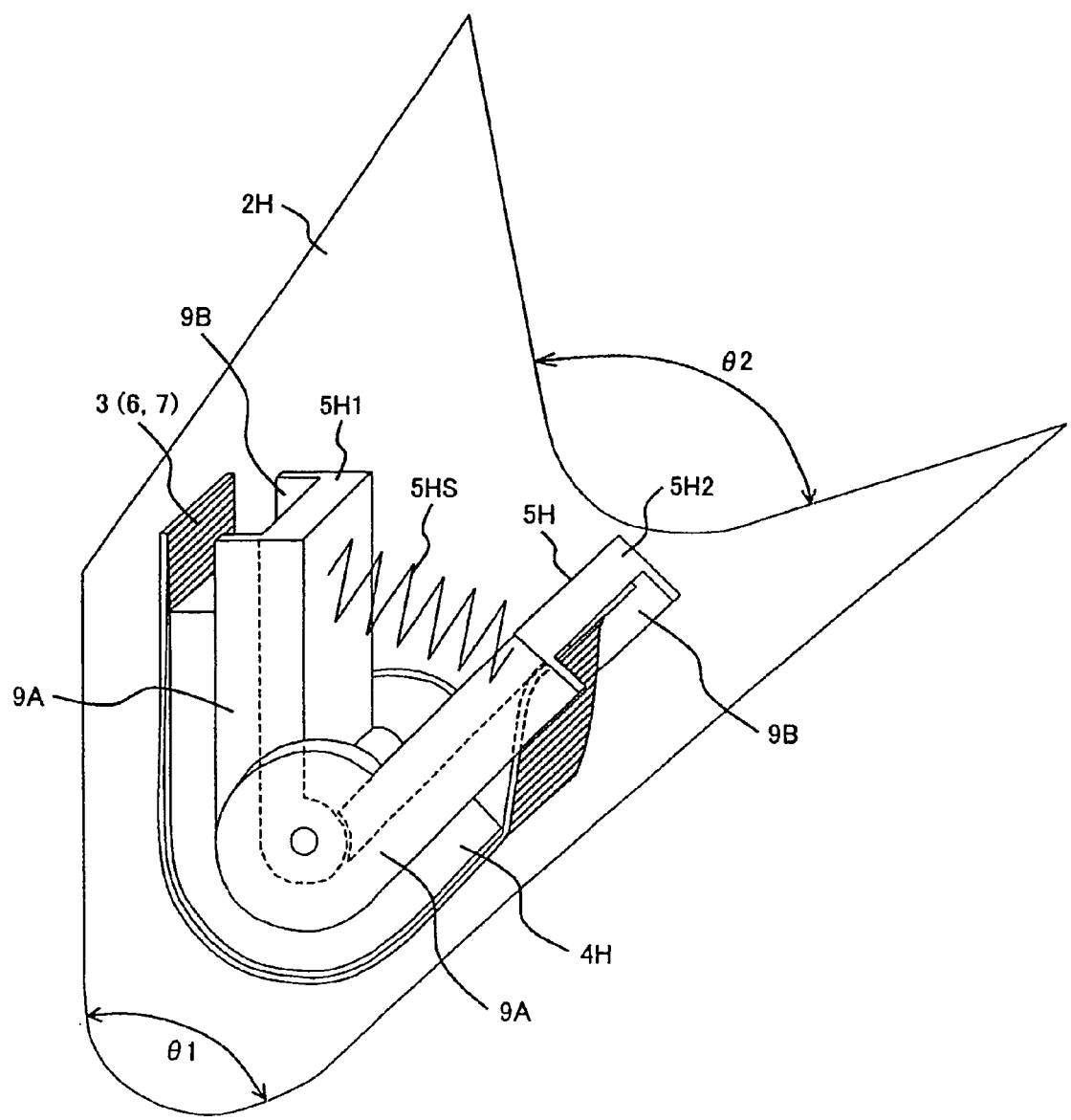
FIG. 11 is an oblique projection view showing a ninth embodiment of eddy current testing probe of the invention.

FIG. 11 shows the ninth embodiment corresponding to the eddy current testing probe 1H usable in a case where an angle of a concave surface of a test article 2H changes continuously from θ1 to θ2 along a moving direction of the eddy current testing probe 1H. The eddy current testing probe 1H has a pressing member 5H having V-shape, an elastic member 4H arranged on a convex surface of the pressing member 5H, and the flaw detecting sensor 3 attached onto the convex surface of the elastic member 4H by the adhesive or the like, the pressing member 5H has a pair of pressing portions 5H1 and 5H2 connected to each other by a hinge at a peak of the V-shape, a compression spring 5HS is arranged between the pressing portions 5H1 and 5H2, and the protruding parts 9A and 9B protrude from the pressing member 5H adjacently to the elastic member 4H.

By urging the pressing member 5H of the above eddy current testing probe 1H, the pressing member 5H presses through the elastic member 4H the flaw detecting sensor 3 against the concave surface of the test article 2H. When the elastic member 4H is deformed to a certain extent by the pressing member 5H, the protruding parts 9A and 9B contact the surface of the test article 2H so that the elastic member 4H is prevented from being further deformed, whereby the deformation or damage of the coils (not shown) of the flaw detecting sensor 3 is prevented from being caused by a significant deformation of the elastic member 4G. When the angle of the concave surface of the test article 2H changes continuously from the narrow angle θ1 to the wide angle θ2 along the moving direction of the flaw detecting sensor 3, the angle between the pressing portions 5H1 and 5H2 is continuously changed by the spring force of the compression spring 5HS in accordance with the change of the angle of the concave surface, so that the flaw detecting sensor 3 can closely contact the concave surface of the test article 2H along the angle thereof.

Incidentally, in FIGS. 10 and 11, the common reference sign used in the other embodiment denotes the identical member, and an explanation thereon is not repeated.

Figure 12:
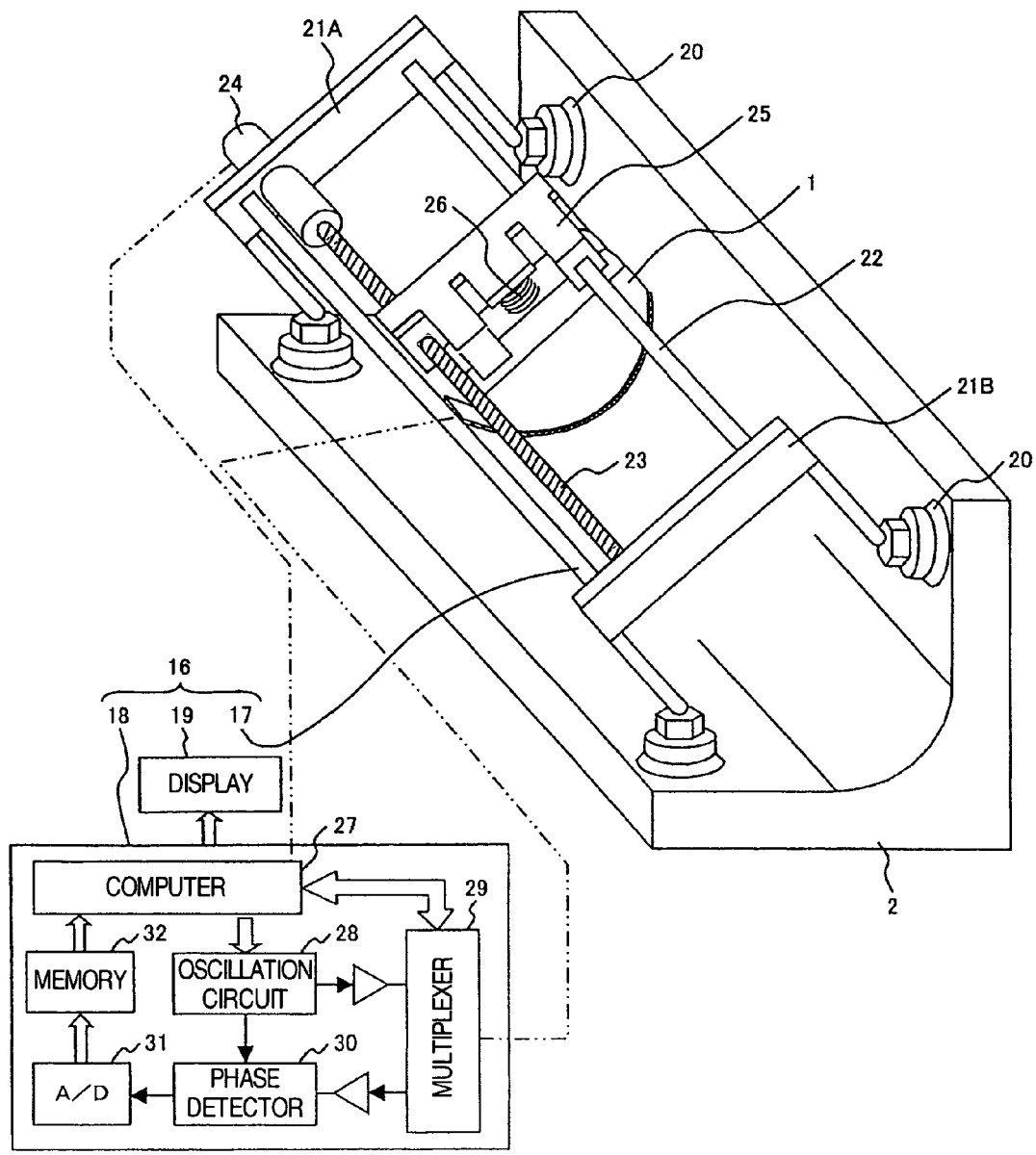
FIG. 12 is a schematic view showing an embodiment of eddy current testing apparatus of the invention.

Next, an embodiment of eddy current testing apparatus in which the above mentioned eddy current testing probes are usable is explained on the basis of FIG. 12.

The eddy current testing apparatus 16 of embodiment has a scanner 17 for scanning the surface of the test article 2 with the eddy current testing probe, a controller for controlling the scanner 17 and a display 19 for displaying a result of the flaw detection.

The scanner 17 includes a pair of frames 21A and 21B having respective fixing members 20 of suction cups or magnets for fixing the frames to the surface of the test article 2, a guide rail 22 extending between the frames 21A and 21B, a screw rod 23 supported in a rotatable manner and extending parallel to the guide rail 22 between the frames 21A and 21B, a motor 24 for rotationally driving the screw rod 23, a scanner head 25 supported by the guide rail 22 and engaging with the screw rod 23, and the eddy current testing probe 1 (1A, 1B, 1C, 1E or 1F) supported on the scanner head 25 through a pressing spring 26.

The controller 18 has a computer 27 for changing sequentially the energized one of the coils 7 of the eddy current testing probe 1, an oscillation circuit 28 for generating voltage along an order from the computer 27, a multiplexer 29 for changing the energized one of the coils 7 to which the voltage from the oscillation circuit 28 is supplied, a phase adjustor 30 for receiving through the multiplexer 29 a flaw detection signal from one(s) of the coils 7 for the flaw detection (for generating an eddy current corresponding to the flaw detection signal induced in accordance with a change in magnetic flux or field passing through the one(s) of the coils 7 for the flaw detection and supplied from the test article magnetically excited by the energized one(s) of the coils 7) selected by making reference to the voltage from the oscillation circuit 28, an A/D converter 31 for A/D conversion of the signal from the phase adjustor 30, and a memory for recording sequentially electronic data corresponding to the signal from the A/D converter 31.

The display displays in accordance with an instruction from the computer the electronic data recorded by the memory 32.

In the eddy current testing apparatus 16, the screw rod 23 is rotationally driven by the motor 24 in accordance with the instruction from the computer after the sequential flaw detection with changing a condition of each of the coils 7 between the energizing condition and the detecting condition is completed. The scanner head 25 is moved by the rotation of the screw rod 23 on the surface of the test article 2 along the guide rail 22 so that a next flaw detection can be performed.

In this structure, the computer 27, oscillation circuit 28 and multiplexer 29 correspond to a coil switching device of the invention, the multiplexer 29, phase adjustor 30, A/D converter 31, memory 32, computer 27 and display 19 correspond to a display of the invention for displaying the flaw detection signal, the computer 27, motor 24, screw rod 23 and guide rail 22 correspond to a moving device of the invention for moving the eddy current testing probe on the test article in single direction.

Incidentally, in the eddy current testing apparatus 16, for pressing the eddy current testing probe against the test article 2, the pressing spring 26 may be replaced by a combination of another motor and another screw rod. In this case, the force for pressing the eddy current testing probe can be limited by controlling the rotation of the another motor so that the combination of the another motor and the another screw rod becomes the movement limiting member of the invention for limiting the movement of the pressing member.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. An eddy current testing probe comprising, a flexible substrate adapted to face to a surface of a test article, a plurality of coils which are fixed to the flexible substrate and energized one of which coils is capable of being changed sequentially, a pressing member for pressing the substrate toward the test article, an elastic member arranged between the substrate and the pressing member, and a coil deformation preventing member for preventing the coils from being deformed by the elastic member.

2. An eddy current testing probe according to claim 1, wherein the pressing member has a transformable part to change a shape of the flexible substrate in accordance with a shape of the surface of the test article.

3. An eddy current testing probe comprising, a flexible substrate adapted to face to a surface of a test article, a plurality of coils which are fixed to the flexible substrate and energized one of which coils is capable of being changed sequentially, a pressing member for pressing the substrate toward the test article, an elastic member arranged between the substrate and the pressing member, and a movement limiting member for limiting a movement of the pressing member toward the test article.

4. An eddy current testing probe according to claim 3, wherein the movement limiting member is connected to the pressing member.

5. An eddy current testing probe according to claim 3, wherein the movement limiting member is connected to the elastic member.

6. An eddy current testing probe according to claim 3, wherein the elastic member is porous.

7. An eddy current testing probe according to claim 3, wherein the elastic member has a space receiving the coils with a clearance between the elastic member and the coils so that the coils are prevented from contacting the elastic member.

8. An eddy current testing probe according to claim 3, wherein the elastic member and the flexible substrate are sewed together.

9. An eddy current testing probe according to claim 3, wherein the pressing member has a transformable part to change a shape of the flexible substrate in accordance with a shape of the surface of the test article.

10. An eddy current testing probe according to claim 3, wherein the movement limiting member has a front surface arranged to face to the surface of the test article with a clearance between the front surface and the surface of the test article when the substrate contacts the surface of the test article and an elastic displacement of the substrate with respect to the pressing member through the elastic member is prevented from increasing to a predetermined value and arranged to contact the surface of the test article when the substrate contacts the surface of the test article and the elastic displacement of the substrate with respect to the pressing member through the elastic member increases to the predetermined value.

11. An eddy current testing probe according to claim 10, wherein a spring constant of the elastic displacement of the substrate with respect to the pressing member through the elastic member in a direction of a pressing force applied from the pressing member to the substrate and the front surface to contact the surface of the test article is smaller than a spring constant of an elastic displacement of the front surface with respect to the pressing member in the direction.

12. An eddy current testing probe according to claim 10, wherein the elastic member is poriferous.

13. An eddy current testing apparatus, comprising an eddy current testing probe including a flexible substrate adapted to face to a surface of a test article, a plurality of coils which are fixed to the flexible substrate and energized one of which coils is capable of being changed sequentially, a pressing member for pressing the substrate toward the test article, an elastic member arranged between the substrate and the pressing member, and a movement limiting member for limiting a movement of the pressing member toward the test article, a coil switching device for changing the energized one of the coils sequentially, a display for displaying a flaw detection signal from detecting one of the coils for flaw detection, and a drive member for moving the eddy current testing probe on the test article.

* * * * *